United States Patent
Schierle-Arndt et al.

(10) Patent No.: US 6,657,091 B2
(45) Date of Patent: Dec. 2, 2003

(54) CATALYTIC PREPARATION OF ALKALI METAL ALKOXIDES

(75) Inventors: Kerstin Schierle-Arndt, Zwingenberg (DE); Hans-Josef Sterzel, Dannstadt-Schauernheim (DE); Dieter Schläfer, Ludwigshafen (DE); Josef Guth, Freinsheim (DE); Holger Friedrich, Bobenheim-Roxheim (DE); Peter Zehner, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 71 days.

(21) Appl. No.: 09/964,798

(22) Filed: Sep. 28, 2001

(65) Prior Publication Data

US 2002/0062050 A1 May 23, 2002

(30) Foreign Application Priority Data

Oct. 6, 2000 (DE) .......................... 100 50 015

(51) Int. Cl.⁷ .................. C07C 31/30; C01D 15/00; C01D 1/32
(52) U.S. Cl. .................. 568/851; 423/180; 423/192
(58) Field of Search .................. 568/851; 423/180, 423/192

(56) References Cited

U.S. PATENT DOCUMENTS

| 2,069,403 A | 2/1937 | Lewis | 260/156 |
|---|---|---|---|
| 2,336,045 A | 12/1943 | Taylor | 204/72 |
| 2,761,880 A | 9/1956 | Gerber et al. | 260/632 |
| 4,596,895 A | 6/1986 | Auschner et al. | 568/851 |
| 5,262,133 A | 11/1993 | Adams et al. | 423/180 |
| 5,942,647 A | 8/1999 | Hamann et al. | 568/851 |
| 6,150,569 A | 11/2000 | Hamann et al. | 568/851 |
| 6,191,319 B1 | 2/2001 | Hamann et al. | 568/851 |

FOREIGN PATENT DOCUMENTS

| DE | 973 323 | 1/1960 |
|---|---|---|
| DE | 810 193 | 12/1997 |
| DE | 198 02 013 | 7/1999 |
| EP | 177 768 | 4/1986 |
| EP | 1 018 499 | 7/2000 |

OTHER PUBLICATIONS

MacMullin "By–Products of Amalgam–Type Chlorine Cells" Chem. Eng. Progress vol. 46 No. 9 (1950) pp. 440–455.

Ullmann's Encyclopedia of Industrial Chemistry vol. A1 (1985) pp. 279–303.

*Primary Examiner*—Johann Richter
*Assistant Examiner*—Sikarl A. Witherspoon
(74) *Attorney, Agent, or Firm*—Keil & Weinkauf

(57) ABSTRACT

Alkali metal alkoxides are prepared by reacting alkali metal amalgam with alcohol in the presence of a catalyst comprising iron having a carbon content of at least 0.3% by weight.

9 Claims, No Drawings

CATALYTIC PREPARATION OF ALKALI METAL ALKOXIDES

The present invention relates to a process for the catalytic preparation of alkali metal alkoxides by reacting alkali metal amalgam with an alcohol in the presence of a catalyst.

Alkali metal alkoxides (systematic name: "alkali metal alkanolates") are well known reagents in organic chemistry. They are used where strong bases are required as reactants, and are employed as catalysts in certain reactions. Alkali metal alkoxides produced and used in relatively large amounts are virtually exclusively aliphatic alkoxides of lithium, sodium and potassium having from 1 to 4 carbon atoms in the alkyl radical of the alcohol, in particular lithium, sodium and potassium methoxide, ethoxide, n-propoxide, isopropoxide, n-butoxide and tert-butoxide. A number of methods of preparing alkali metal alkoxides are known. The most widespread are the reaction of the alkali metal with the alcohol so as to liberate hydrogen and the reaction of the alkali metal hydroxide with the alcohol and removal of the water formed as by-product. A process specifically employed for preparing higher alkali metal alkoxides is the reaction of an alkali metal methoxide or ethoxide with a higher alcohol and removal of methanol or ethanol. This latter process and the reaction of alkali metal hydroxide with alcohol and removal of the by-product water are frequently inferior to the direct reaction of alkali metal with alcohol from an economic point of view, since they are comparatively energy-intensive.

The direct reaction of an alkali metal with an alcohol is the simplest method of preparing alkali metal alkoxides. The reactivity of the alkali metals increases in the order lithium, sodium, potassium, rubidium and cesium, and the reactivity of the alcohols decreases with increasing molecular weight of the alcohol and increasing degree of branching of the alkyl radical. The reaction is advantageously carried out using a dispersion of the alkali metal in an inert solvent or using alkali metal amalgam. A general overview of aliphatic alkali metal alkoxides, their preparation and use is given, for example, in Ullmann's Encyclopedia of Industrial Chemistry, Fifth Edition, Volume A1, Weinheim 1985, as item 3 under the keyword "Alcohols, Aliphatic". An overview of the industrial production of alkali metal alkoxides from alkali amalgam and reaction apparatuses used for this purpose is given, for example, in; R. B. MacMullin "By-products of Amalgam-type Chlorine Cell", Chemical Engineering Progress September 1950, pp. 440–455 , 448.

In the preparation of higher alkali metal alkoxides (which for the purposes of the present invention are alkoxides having at least 3 carbon atoms in the organic radical), the method described by MacMullin, loc. cit., can be employed but is frequently economically unsatisfactory because of low reaction rates. Processes which make a higher space-time yield possible by use of a catalyst have therefore been developed.

Such catalytic methods have been known for a long time. Thus, U.S. Pat. No. 2,069,403 teaches a process for preparing alkali metal alkoxides by reacting alkali metal amalgam with alcohols having up to 4 carbon atoms, in which the reaction is carried out in the presence of a catalyst comprising graphite or iron-chromium alloys which may, if desired, further comprise alloying constituents such as nickel, molybdenum, tungsten or manganese. A specific embodiment of this process and a typical reactor are described in U.S. Pat. No. 2,336,045. Here, the amalgam and the alcohol are passed in countercurrent through the reactor in which the catalyst is present in the form of packing. In these documents, the catalyst is referred to as "electrode".

In the process of U.S. Pat. No. 2,761,880, the alkali metal amalgam is fed in in the form of a dispersion in countercurrent to the alcohol, with electrode graphite, activated carbon and/or iron turnings additionally being used as catalyst. A preferred catalyst is a mixture of activated carbon with 10–20 of iron turnings. DE-A-973 323 discloses a catalyst comprising 0.1–10% by weight of a metal of the iron group, in particular iron or nickel, on a graphite support. EP-A-177 768 proposes a catalyst comprising heavy metal oxide or oxides, in particular a mixture of nickel oxide and molybdenum oxide, applied to the surface of a particulate anthracite support for preparing alkali metal alkoxides. U.S. Pat. No. 5,262,133 teaches the use of tungsten carbide, iron on carbon supports, iridium, ruthenium or mixtures thereof as catalyst. EP-A-810 193 discloses catalysts comprising carbides and nitrides of chromium, molybdenum or tungsten and also catalysts comprising titanium carbide. In the process of DE-A-198 02 013, the catalysts used comprise transition metal carbides, nitrides or carbonitrides, in particular molybdenum carbide or tungsten carbide, in powder form, and in the process of EP-A-1 018 499 this powder catalyst is suspended by action of ultrasound.

However, the space-time yield is still unsatisfactory in many known processes and the known processes giving a relatively high space-time yield require catalysts which are comparatively expensive because of their short operating life or high price. It is an object of the present invention to find a simpler, more economically satisfactory process which makes possible a very high space-time yield and makes do with an inexpensive catalyst.

We have found that this object is achieved by a process for preparing alkali metal alkoxides by reacting alkali metal amalgam with alcohol in the presence of a catalyst comprising iron having a carbon content of at least 0.3% by weight.

The catalyst used in the process of the present invention is inexpensive, has a high operating life and makes it possible to achieve high space-time yields. A particular advantage of the process of the present invention is that it can be carried out without problems in existing reactors so that no conversion of existing plants is necessary.

In the process of the present invention, lithium, sodium, potassium, rubidium or cesium is used as alkali metal. Preference is given to using sodium or potassium. The alkali metal amalgam in which the alkali metal used is present can be produced by any known process for preparing alkali metal amalgam, for example by mixing alkali metal and mercury, but is usually prepared in a known manner by electrolysis of a solution of an appropriate salt, for example a halide, in general the alkali metal chloride, in an electrolysis cell. A type of electrolysis cell which is particularly suitable for this purpose is that in which the known amalgam process for preparing chlorine and sodium hydroxide is usually carried out. The amalgam generally contains at least 0.05% by weight of alkali metal, preferably at least 0.1% by weight and particularly preferably at least 0.2% by weight. It generally contains not more than 1% by weight of alkali metal, preferably not more than 0.7% by weight and particularly preferably not more than 0.5% by weight.

As alcohol, it is in principle possible to use any compound having a hydroxy group attached to a carbon-containing radical. Use is generally made of aliphatic alcohols, in particular those having a straight-chain or branched alkyl radical having from 1 to 8 carbon atoms. Preference is given to using primary, secondary or tertiary alcohols having from one to five carbon atoms, particularly preferably from one to four carbon atoms. Examples of alcohols used in the process of the present invention are methanol, ethanol, n-propanol, isopropanol, n-butanol, 2-butanol (sec-butanol), 2-methyl-1-propanol (isobutanol), 2-methyl-2-propanol (tert-butanol), 1-, 2- or 3-pentanol, neopentanol, tert-pentanol, hexanol, heptanol or octanol.

The most economically important and therefore preferred products of the process of the present invention are sodium and potassium methoxide, ethoxide and tert-butoxide. Preference is therefore given to using methanol, ethanol or tert-butanol.

It is likewised possible to use alcohols having more than one hydroxy group, for example glycol.

After the alkali metal alkoxides have been formed by replacement of the hydrogen atom of the hydroxy group of the alcohol by the alkali metal, the alkyl radical of the alcohol used is directly present in the alkali metal alkoxide.

The process of the present invention is particularly suitable for preparing sodium methoxide, potassium methoxide, sodium ethoxide, potassium ethoxide, sodium tert-butoxide and potassium tert-butoxide.

The catalyst comprises iron having a carbon content of at least 0.3% by weight. The iron preferably contains at least 0.5% by weight of carbon, particularly preferably at least 1% by weight of carbon. The carbon content of the iron is generally not more than 4% by weight. The catalyst is not a mixture of macroscopic iron particles and macroscopic carbon particles, but rather an iron-carbon alloy and therefore contains carbon incorporated into the microstructure, for example in the form of a solid solution or as carbon precipitated homogeneously in the metal matrix. A carbon content above 4% by weight is generally no longer present as a solution in the iron or as precipitates homogeneously distributed in the microstructure, but rather in the form of relatively large, loose or inhomogeneously distributed carbon particles. These have no significant influence on the process.

Apart from carbon, further constituents may be present in the iron, for example typical alloying elements or residues of additives used in the production of iron or steel, e.g. silicon, sulfur, chromium, manganese, molybdenum and/or phosphorus. If carbonyl iron is used, oxygen and/or nitrogen may also be present as a result of the method of preparation. Apart from the unavoidable impurities originating from iron production (for example residues of the additives customarily used there or oxygen and/or nitrogen in the case of carbonyl iron), the carbon-containing iron used in the process of the present invention preferably contains no further deliberately added constituents.

The active composition of the catalyst may further comprise, in addition to the carbon-containing iron, other constituents which chemically influence its catalytic properties, for example promoters or other known catalytically active components. Preference is given to using a catalyst whose active composition contains such secondary components to only a minor extent, i.e. consists essentially of iron containing at least 0.3% by weight of carbon. Particular preference is given to using a catalyst whose active composition comprises iron containing at least 0.3% by weight of carbon and only unavoidable impurities.

The active composition may be applied to a catalyst support, for example carbon, in particular graphite or anthracite, but is preferably used as support-free catalyst.

Preference is given to using a catalyst which consists essentially of carbon-containing iron having a carbon content of at least 0.3% by weight. Particular preference is given to using a catalyst consisting of carbon-containing iron having a carbon content of at least 0.3% by weight and further comprising only unavoidable impurities originating from iron production but no deliberately added amounts of further constituents. Typical compositions are, for example, 3.8% by weight of carbon, 2.1% by weight of silicon, traces of sulfur, chromium, manganese, molybdenum and phosphorus, balance iron, or 3.3% by weight of carbon, 2.5% by weight of silicon, traces of sulfur, chromium, manganese, molybdenum and phosphorus, balance iron, or 1.8% by weight of carbon, 1.7% by weight of nitrogen, 0.2% by weight of oxygen, balance iron.

A catalyst which is preferably used in the process of the present invention is cast iron, namely castable carbon-containing iron having a carbon content of from 2 to 4% by weight, in particular gray cast iron which has a silicon content of from about 2 to 3% by weight due to the addition of silicate and in the case of which slow cooling of the initially liquid iron results in precipitation of carbon, for instance as lamella or spherical graphite, in the microstructure, so that fracture surfaces appear gray (for definitions of the terms, see Römpp Chemie Lexikon, Thieme Verlag, Stuttgart 1990, Volume 2, ISBN 3-13-734709-2, keyword "Gußeisen"). Production and processing of cast iron are well known.

Another catalyst whose use is likewise preferred in the process of the present invention is carbonyl iron having a carbon content of at least 0.3% by weight, in particular at least 1% by weight. Carbonyl iron is iron which is prepared by decomposition of iron carbonyl and whose carbon, nitrogen and oxygen contents can be set in a known manner by appropriate choice of parameters in the decomposition and/or by after-treatment (cf., for example, Ullmann's Encyclopedia of Industrial Chemistry, Fifth Edition, Volume A14, Weinheim 1989, as item 3.5 Iron Pentacarbonyl/Uses under the keyword "Iron compounds", and the references cited therein). Preparation and processing of carbonyl iron are well known.

The catalytic activity of the catalyst can be increased further by treatment with mineral acid, for example sulfuric acid, nitric acid or hydrochloric acid, preferably hydrochloric acid or nitric acid, before it is used. For this purpose, the catalyst is brought into contact with the acid. The concentration of the acid is generally at least 1% by weight, preferably at least 3% by weight and particularly preferably at least 5% by weight. The concentration is generally not more than 30% by weight, preferably not more than 20% by weight and particularly preferably not more than 15% by weight. 10% strength by weight hydrochloric acid and 10% strength by weight nitric acid are particularly useful. The acid treatment of the catalyst generally takes at least one minute, preferably at least 5 minutes and particularly preferably at least 10 minutes. It is generally complete after not more than two hours, preferably after not more than 90 minutes and particularly preferably after not more than one hour. The temperature is generally at least 0° C., preferably at least 10° C. and particularly preferably at least 20° C. It is generally not more than 100° C., preferably not more than 60° C. and particularly preferably not more than 40° C. For the acid treatment, the catalyst is covered with the acid in a reaction vessel, for example the reactor in which the reaction of amalgam with alcohol is carried out. If desired, the acid can also be moved through the reaction vessel. This treatment usually results in formation of a little hydrogen which should be removed as in the subsequent reaction itself. If desired, the catalyst is rinsed with water after the acid treatment. This acid treatment is also suitable for reactivating deactivated catalysts.

The catalyst is used as powder or preferably in the form of larger particles. Particle sizes having dimensions in all three spatial directions of at least 0.5 mm, preferably 1 mm, and not more than 20 mm, preferably not more than 10 mm, are generally well suited for use in customary reactors. To avoid the formation of regular three-dimensional structures, preference is given to using irregularly shaped particles. These can be produced by crushing or machining of massive material, for example commercial cast iron. It is particularly convenient to use small iron articles of cast iron as catalyst, for example cast iron screws or cast iron nuts. Finely divided iron, for example commercial carbonyl iron powder, can be shaped to form catalyst particles of the desired size by any known shaping method, for example by pressing and/or sintering and, if appropriate, crushing or machining a larger shaped body produced in this way.

The catalyst is used in a customary reactor.

To carry out the process of the present invention, the alkali metal amalgam and the alcohol are reacted in the reactor filled with catalyst. The alcohol is usually used in excess, so that a solution of the alkali metal alkoxide in the corresponding alcohol is prepared, since the separation of the alkali metal alkoxides, which in pure form are solid at ambient temperature, from the mercury or, in the case of incomplete reaction of the alkali metal, the amalgam depleted in alkali metal would otherwise be cumbersome to carry out. The process can be carried out batchwise or continuously; a continuous process is generally more economical. In such a process, the alcohol and the amalgam are typically passed continuously in countercurrent through the reactor filled with catalyst.

The mercury leaving the reactor is returned to the process for preparing alkali metal amalgam. In the case of incomplete reaction of the alkali metal, the amalgam which has been depleted in alkali metal can likewisse be returned to the process for preparing alkali metal amalgam, but it can, if desired, also be returned to the reactor until the desired alkali metal conversion has been achieved. It is likewise possible to react the depleted amalgam leaving the reactor with another alcohol to form an alkoxide and mercury or with water to form alkali metal hydroxide and mercury.

The alkali metal alkoxide solution leaving the reactor is either used directly or the alkali metal alkoxide present therein is isolated by customary methods (for example by evaporation of the solution and, if desired, subsequent purification, for example by recrystallization), or it is returned to the reactor until the desired concentration of alkali metal alkoxide has been reached. The flow of alcohol through the reactor is preferably set so that an alkoxide solution of the desired concentration is taken from the reactor without recirculation.

The reaction temperature is generally at least 0° C., preferably at least 10° C. and particularly preferably at least 20° C. Since the alkali metal alkoxide can decompose at excessively high temperatures, the reaction temperature is subject to restriction; its upper limit is the temperature at which decomposition results in product losses which are no longer economically tolerable. The reaction is frequently and preferably carried out at the boiling point of the alcohol used.

It may be necessary, especially in the reaction of relatively reactive alcohols (whose reactivity is known to decrease with increasing molecular weight of the alcohol and with increasing degree of branching of the substituent), for the heat of reaction to be removed, which is carried out by means of customary cooling facilities. The heat of the reaction is removed, for example, by means of cooling coils in or around the reactor, passing the streams leaving the reactor through heat exchangers or by evaporative or reflux cooling resulting from alcohol boiling off. The hydrogen formed as by-product is taken in gaseous form from the reactor and is disposed of, for example by incineration, or preferably used further, for example as hydrogenation hydrogen for hydrogenation reactions.

The amount of catalyst (i.e. also the reactor size), the residence time of the reactants in the reactor and the reaction temperature are chosen so that any decomposition of starting materials or products is avoided or remains within economically tolerable limits.

EXAMPLES

Experimental Procedure

In a stirred apparatus which had been flushed with argon, 2000 g of mercury having a potassium content of 0.3% by weight were reacted with 200 g of tert-butanol in the presence of a catalyst. The reaction mixture was stirred (300 revolutions per minute) and the heat of reaction was removed by condensation of vaporized tert-butanol by means of a reflux condenser. The conversions and yields were subsequently determined. The results of the experiments are summarized in Table 1.

Example 1

The catalyst used consisted of 20 g of carbon-containing iron (3.8% by weight of carbon, 2.1% by weight of silicon, traces of sulfur, chromium, manganese, molybdenum and phosphorus, balance iron, particle size: 0–3 mm).

Example 2

100 g of cast iron nuts (5.5×7 mm) were used as catalyst.

Example 3

100 g of sintered and subsequently crushed carbonyl iron (particle size: 2–4 mm) having a carbon content of 1.4% by weight were used as catalyst.

Comparative Example C1

20 g of molybdenum carbide (particle size: about 2 μm) were used as catalyst.

Comparative Example C2

20 g of electrode graphite (0–40 μm) were used as catalyst.

Comparative Example C3

50 g of iron (iron powder prepared by thermal decomposition of iron pentacarbonyl and having a carbon content of less than 0.2% by weight, particle size>500 μm, "oversize" from industrial carbonyl iron production) were initially used as catalyst. After a reaction time of 8.3 hours, another 150 g of this catalyst were added, and after a total reaction time of 16.8 hours, 20 g of electrode graphite were additionally added.

TABLE 1

| Example | 1 | 2 | 3 | C1 | C2 | C3 | | |
|---|---|---|---|---|---|---|---|---|
| Reaction time [hours] | 9 | 14 | 14 | 10 | 13 | 8.3 | 16.8 | 25.8 |
| Potassium conversion [mol %] | 100 | 80 | 79 | 100 | 40 | 3 | 5.3 | 9.4 |
| Yield [mol %] | 100 | 80 | 79 | 100 | 40 | 3 | 5.1 | 8.6 |

Example 1 shows that the catalyst used according to the present invention gives, in a shorter reaction time, the same yields as when using the expensive molybdenum carbide (Comparative Example C1). Even the particularly convenient and inexpensive cast iron nuts represent a significantly more active catalyst (higher conversion at comparable reaction time) than the known electrode graphite catalyst (Comparative Example C2). The same applies to the carbonyl iron of experiment 3. Comparative Example C3 shows that the use of pure iron or a macroscopic mixture of pure iron and carbon has a far lower catalytic activity than the carbon-containing iron used according to the present invention.

We claim:

1. A process for preparing alkali metal alkoxides by reacting alkali metal amalgam with an alcohol in the presence of a catalyst comprising iron in the form of a metallic matrix having a content of dispersed carbon of at least 0.3% by weight.

2. The process of claim 1, wherein the catalyst consists essentially of iron in the form of a metallic matrix having a content of dispersed carbon of from 0.3% to 4% weight.

3. The process of claim 2, wherein the catalyst consists of iron in the form of a metallic matrix having a content of dispersed carbon of at least 0.3% by weight and contains no further constituents apart from unavoidable impurities originating from iron production.

4. The process of claim 3, wherein the catalyst is carbonyl iron.

5. The process of claim 3, wherein the catalyst is cast iron having a carbon content of from 2 to 4% by weight.

6. The process of claim 1, wherein an aliphatic primary, secondary or tertiary alcohol having from 1 to 8 carbon atoms in the alkyl radical is used.

7. The process of claim 6, wherein methanol, ethanol or tert-butanol is used.

8. The process of claim 6, wherein sodium or potassium is used as alkali metal.

9. A process for preparing alkali metal alkoxides by reacting alkali metal amalgam with an alcohol in the presence of a catalyst comprising iron in the form of a metallic matrix having a content of dispersed carbon of at least 0.3% by weight, wherein the catalyst is treated with mineral acid before use.

* * * * *